(12) United States Patent
Shi et al.

(10) Patent No.: US 10,275,659 B2
(45) Date of Patent: Apr. 30, 2019

(54) COMPUTER VISION AND SENSOR ASSISTED CONTAMINATION TRACKING

(71) Applicant: Intel Corporation, Santa Clara, CA (US)

(72) Inventors: Meng Shi, Hillsboro, OR (US); Carl S. Marshall, Portland, OR (US); Glen J. Anderson, Beaverton, OR (US); Selvakumar Paneer, Portland, OR (US); Anthony G Lamarca, Seattle, WA (US); Mark J. Abel, Portland, OR (US); Giuseppe Raffa, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 15/475,423

(22) Filed: Mar. 31, 2017

(65) Prior Publication Data

US 2018/0285649 A1 Oct. 4, 2018

(51) Int. Cl.
| | |
|---|---|
| *G06K 9/00* | (2006.01) |
| *G01N 33/12* | (2006.01) |
| *H04N 7/18* | (2006.01) |
| *G06K 9/62* | (2006.01) |
| *H04L 29/08* | (2006.01) |
| *G08B 21/12* | (2006.01) |

(52) U.S. Cl.
CPC ........ *G06K 9/00771* (2013.01); *G01N 33/12* (2013.01); *G06K 9/00335* (2013.01); *G06K 9/6202* (2013.01); *G08B 21/12* (2013.01); *H04L 67/306* (2013.01); *H04N 7/183* (2013.01); *G06K 2209/17* (2013.01)

(58) Field of Classification Search
CPC ........... G06K 9/00771; G06K 9/00335; G06K 9/6202; G06K 2209/17; G01N 33/12; G08B 21/12; H04L 67/306; H04N 7/183
See application file for complete search history.

(56) References Cited

U.S. PATENT DOCUMENTS

| | | | |
|---|---|---|---|
| 2014/0236759 A1* | 8/2014 | Mirabile | ............ G06Q 30/0633 705/26.8 |
| 2014/0244344 A1* | 8/2014 | Bilet | .................. G06Q 10/0635 705/7.28 |

* cited by examiner

*Primary Examiner* — Amara Abdi
(74) *Attorney, Agent, or Firm* — Schwegman Lundberg & Woessner, P.A.

(57) ABSTRACT

Systems and techniques for computer vision and sensor assisted contamination tracking are described herein. It may be identified that a food item has moved to a monitored area using computer vision. Sensor readings may be obtained from a sensor array. A contamination of the food item may be determined using the sensor readings. The contamination of the food item may be associated with a contamination area in the monitored area using the computer vision. A notification may be output for display in the contamination area indicating the contamination.

24 Claims, 5 Drawing Sheets

COMPUTER VISION AND SENSOR ASSISTED CONTAMINATION TRACKING

TECHNICAL FIELD

Embodiments described herein generally relate to contamination tracking and, in some embodiments, more specifically to computer vision and sensor assisted contamination tracking.

BACKGROUND

Food contamination may be a health hazard. Food contamination may result from a variety of factors such as, for example, food being in contact with a hazardous substance (e.g., pathogen, radiation, hazardous chemical, etc.), being stored at unsafe temperatures allowing bacteria to spread, contacting an allergen, etc. Knowing that food is contaminated may reduce instances of foodborne illnesses.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Food contamination is a concern faced by people every day. Controlling food contamination may be important to food-related businesses. For example, in the restaurant sector, food poisoning outbreaks may cause financial loses and customer loyalty loses for an affected restaurant and/or restaurant chain. Individuals may benefit from better management of food contamination through better health and saving money by reducing food waste.

There may be traditional sensors available to monitor food contamination. However, the traditional sensors may only track contamination at a specific point in time, may be difficult to use without special training, and may require complicated installation. Traditional sensors may be inconvenient which may result in reduced usage. For example, using traditional sensors, testing food contamination when preparing a meal may involve washing the food tester's hands, choosing the right sensors, setting up, and performing the test before getting results. Some traditional sensors may need to continually retested (e.g., calibrated, etc.) to obtain accurate results. These issues may limit the usage of traditional sensors in a kitchen.

To address the issues with traditional sensors, a camera may be used for object recognition and tracking which may collaborate with other sensors like thermometers and biosensors to keep track of whether food may be contaminated and predicting imminent food contamination. Cameras may track food items, contaminated utensils (e.g., contaminated by contact with raw meat), contaminated hands, and contaminated surfaces. Sensors may be embedded in utensils, surfaces, walls/ceiling, wearables, etc. Projectors and/or other output devices may be used to output suggestions and/or other feedback on and/or near the food that is contaminated or at risk of being contaminated. The output may include, for example, projections, audio, ambient lighting, augmented reality, etc. Thus, people working with food may be better informed of contaminated food and/or food that is at risk of becoming contaminated which may reduce foodborne illness. Machine-learning techniques (e.g., using single implementation, crowd-sourcing, etc.) may allow the output of predictive recommendations for avoiding food contamination over time.

Figure 1:
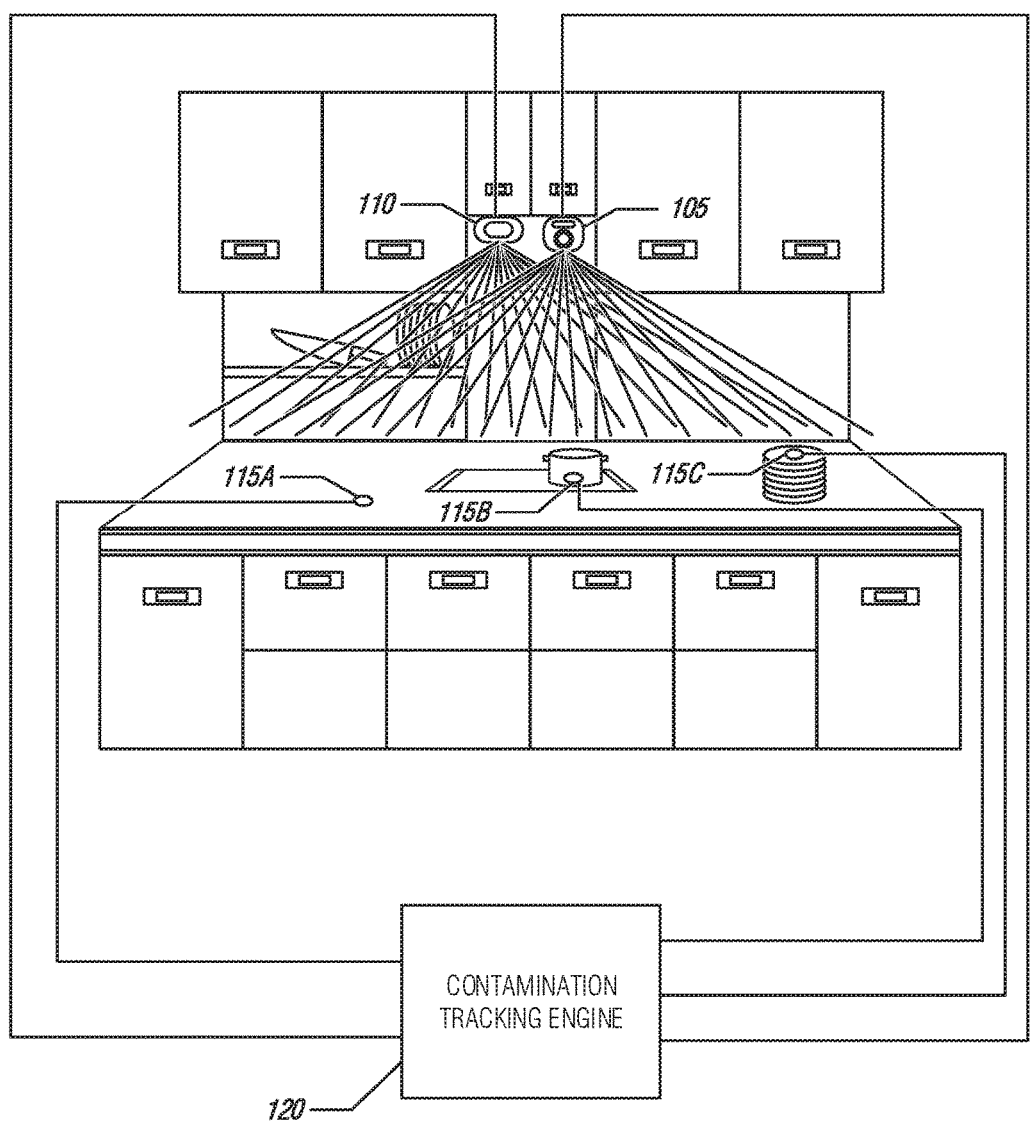
FIG. 1 illustrates a diagram of an example of an environment and system for computer vision and sensor assisted contamination tracking, according to an embodiment.

FIG. 1 is a diagram of an example of an environment 100 and system for computer vision and sensor assisted contamination tracking, according to an embodiment. The environment 100 represents a food preparation area (e.g., a kitchen, etc.); however, the techniques described herein may be applicable to a variety of areas in which food may be subject to contamination such as, for example, a meat processing plant, a food packaging plant, a food assembly line, etc. The environment 100 may include a camera 105, a projector 110, and sensor arrays (e.g., including sensor 115A, sensor 115B, and sensor 115C).

The camera 105 may be a red-green-blue (RGB) camera, a RGB depth (RGB-D) camera, etc. The camera 105 may be positioned to observe an area of the environment 100 where food items may be handled. The camera 105 may use computer vision techniques (e.g., object recognition, saliency detection, etc.) to identify and track the movement of food items. For example, a raw chicken may be moved from cold storage to a preparation area and the camera 105 may capture images of the movement of the raw chicken and the computer vision techniques may be used to identify the raw chicken in the captured images and that the raw chicken has moved in the captured images.

The projector 110 may project information for display in the environment 100. The projector 110 may be positioned to project the information on and/or near the food item. Continuing the example from above, the projector 110 may project information on the raw chicken or near the raw chicken in the preparation area. A variety of information such as text and images may be displayed to provide a person working in the preparation area with notifications and/or other information relevant to the handling and/or status of the food item.

The sensor arrays may be placed throughout the preparation area. For example, sensor array 115A may be placed on a surface such as a countertop, sensor array 115B may be placed on a cooking vessel such as a pot, and sensor array 115C may be placed on plate upon which the food item may be placed. The sensor arrays may be portable (e.g., a refrigerator magnet, etc.) and may be placed on a variety of surfaces and/or utensils. For example, sensor arrays may be placed on utensils that may come in contact with the food item such as, for example, a knife, a cutting board, a fork, etc. In some examples, sensor arrays may be embedded in items that may be contacted (e.g., knife handle, bowl, etc.) to detect contact (and corresponding contamination) from potentially contaminated contact (e.g., from a hand, glove, etc.). The sensor arrays may include a variety of sensors such as, for example, a thermometer, a bio sensor (e.g., bacteria sensor, etc.), a radiation sensor, humidity, etc. The sensor arrays may be portable and may be able to be affixed to utensils, work surfaces, etc.

The sensor arrays may monitor the status of the food item. For example, the sensor array 115A may measure bacteria levels and temperature of the raw chicken while it is sitting on a countertop in the preparation area. Additional sensors such as microphones, cameras (e.g., RGB, infrared (IR), etc.), etc. and/or sensor arrays may be placed in the preparation area and/or food storage areas for additional monitoring. For example, an IR camera may be placed on the wall or the ceiling of the preparation area to monitor temperature of the raw chicken and an RGB camera and a thermometer may be placed in a cold storage location to monitor the movement and temperature of stored food items. The camera and the sensor arrays may be time synchronized for congruity of time and location between the camera 105 and the sensor arrays.

The camera 105, projector 110, and sensor arrays 115A, 115B, and 115C, may be communicatively coupled (e.g., via wired network, wireless network, shared bus, etc.) to the contamination tracking engine 120. The contamination tracking engine 120 may work in conjunction with the camera 105 (and cameras placed in storage areas) to identify the food item and movement of the food item. For example, the food item may be identified as a raw chicken coming into the preparation area from cold storage (e.g., identified using a camera or other sensor monitoring the cold storage location) using the camera 105 and computer vision. The contamination tracking engine 120 may determine sensor data corresponding with the food item based on movement of the food item identified using the camera 105 and computer vision. For example, the raw chicken may be identified as being on the countertop and data from the sensor array 115A may be collected and it may be identified that the raw chicken has moved to a pot and data from sensor array 115B may be collected. Thus, the food item may be tracked using different sensor arrays as it moves through the monitored area.

The contamination tracking engine 120 may identify that the identified food item should be tracked. For example, the raw chicken may be identified for special handling while a loaf of bread identified in the preparation area may not be identified for special handling. The contamination tracking engine 120 may select a set of rules (e.g., handling rules, etc.) corresponding to the food item. For example, a set of raw chicken handling rules may be selected for the identified raw chicken. The set of rules may include a variety of rules including, for example, safe handling guidelines from a regulatory authority (e.g., the United States Food and Drug Administration (FDA), United States Department of Agriculture (USDA), etc.), general safe food handling guidelines, and user specified preferences. For example, the set of rules may include rules for tracking the food item, surfaces contacted by the food item, hands of people making contact with the food item, utensils making contact with the food item, and other food items making contact with the food item.

The contamination tracking engine 120 may monitor the food item to determine if the food item has been contaminated. For example, a thermometer included in sensor array 115A may monitor the temperature of the raw chicken and a bio sensor included in the sensor array 115A may monitor bacteria on the raw chicken as it sits on the countertop. The contamination tracking engine 120 may determine that the item has been contaminated using data collected from the sensor arrays and the set of rules. For example, a rule for the raw chicken may include a temperature threshold of 40° and the raw chicken may be determined to be contaminated if temperature data from the sensor array 115A indicates the temperature of the raw chicken to be at or above 40° Fahrenheit. In another example, a rule for the raw chicken may indicate that the presence of salmonella bacteria indicates the raw chicken is contaminated and the raw chicken may be determined to be contaminated because a bio sensor in the sensor array 115C indicates the presence of salmonella bacteria. In some examples, the camera 105 (or another camera) may be used to take images of the food item to identify color changes in the food item. For example, raw chicken may be pink and may change to off white as the chicken transitions from a raw state to a cooked state.

In some examples, it may be determined that the food item is nearing contamination. For example, it may be determined that the raw chicken is nearing contamination when a thermometer in the sensor array 115A indicates the temperature of the raw chicken below 40° Fahrenheit, but is at 35° Fahrenheit and rising. Thus, the contamination tracking engine 120 may determine varying levels of contamination (e.g., pre-contamination, danger zone, contaminated, etc.). For example, the raw chicken may be determined as nearing contamination at 35° Fahrenheit and rising (e.g., as determined by a temperature change rate calculated from an IR camera, etc.), in a danger zone at 40° Fahrenheit, and contaminated after being at or above 40° Fahrenheit for more than 15 minutes. The levels may be defined in the set of rules selected for the food item.

The contamination tracking engine 120 may track other items that have contacted the food item. In some examples, the other items may be continuously tracked while sharing the same monitored area with the food item. In other examples, the other items may be tracked upon determination that the food item has become contaminated. For example, a knife may be used to cut the raw chicken and a rule may indicate that utensils making contact with raw chicken may be limited to contact with raw chicken. Thus, the food item and contacted items may be tracked over time for varying conditions indicating contamination and the potential for contamination.

The contamination tracking engine 120 may generate output in response to a rule. For example, output indicating that the raw chicken is nearing danger zone (e.g., nearing a danger zone temperature, etc.) may be generated. The generated output may be displayed (e.g., by the projector 110, etc.) on and/or near the food item. For example, a notification that the raw chicken is at 35° Fahrenheit and the danger zone temperature is 40° Fahrenheit may be displayed on the raw chicken. In some examples, a rule may indicate a zone around the food item and output may be generated indicating contact restrictions for the zone. For example, a rule may indicate that a two square foot zone be created around a raw chicken and a two square foot outline may be displayed on the countertop centered on the raw chicken with an indication that the zone is limited to contact with raw chicken. In some examples, output may be generated for display on and/or near items and/or surfaces that have been in contact with the food item. For example, output may be generated for display on the knife used to cut the raw chicken indicating that the knife is contaminated and future contact should be limited to raw chicken.

The contamination tracking engine 120 may monitor the food item and other items making contact with the food item to identify if a rule has been violated. For example, the camera 105 may monitor the food preparation area and determine that the knife used to cut the raw chicken has been used to cut a loaf of bread violating a rule indicating future contact of the knife should be limited to raw chicken. The contamination tracking engine 120 may generate output in response to the violation. A variety of outputs may be used to alert a person in the preparation are of the violation such as, for example, video display output may be generated and transmitted for display by the projector 110, an audio message (e.g., tone, recording, etc.) may be generated and output to a speaker in the preparation area, etc. In some examples, output may be generated for display using augmented reality (e.g., virtual reality, etc.). For example, a person working in the preparation area may be wearing an augmented reality display device and output may be generated overlaying an indication of contamination as the person's gaze transitions through the preparation area.

The contamination tracking engine 120 may maintain a history of rules violations (e.g., in a database, storage device, etc.). For example, the rule violation for cutting the loaf of bread with the knife used to cut the raw chicken may be added to the violation history. The contamination tracking engine 120 may maintain a record of actions performed in response to a detected rule violation. For example, the camera 105 may observe the loaf of bread being moved to a trash receptacle in response to an output alert indicating that the knife used to cut raw chicken was used to cut the loaf of bread. In some examples, the contamination tracking engine 120 may use the actions performed in response to the detected rule violation as machine learning input (e.g., training data, etc.) to adjust rules such as those indicating user preferences. For example, a person in the preparation area may routinely disregard (e.g., by failing to return the raw chicken to cold storage, etc.) alerts indicating that the raw chicken is approaching the danger zone and disregard may be used to determine (e.g., using linear regression, etc.) that the alert output should be altered (e.g., reduce output of approaching danger zone notifications, etc.).

In some examples, the contamination tracking engine 120 may, in conjunction with camera 105, identify a person in the preparation area and may determine a corresponding role (e.g., user profile, job role, etc.) for the person. The contamination tracking engine 120 may select the set of rules using the identified role.

In some examples, the contamination tracking engine 120 may identify a person for whom the food item is being prepared. For example, a camera may be monitoring a dining area and "Joe" may be identified as a person for whom the food item is being prepared. The set of rules may be selected and/or modified based on the identification of the person for whom the food item is being prepared. For example, Joe may be allergic to tree nuts and the set of rules for raw chicken may be modified to include no contact between the raw chicken and tree nuts and areas in which tree nuts have been prepared.

The contamination tracking engine 120 may continually monitor the food item and select a new set of rules as the status of the food item changes. For example, identified raw chicken may transition to cooked chicken (e.g., as determined by temperature, observed activity, etc.) and a set of rules for cooked chicken may be selected. Monitoring and alerting may be adjusted based on the newly selected set of rules. For example, messages indicating the cooked chicken should not be allowed to make contact with a raw chicken area and the like may be displayed while the food item is in a cooked chicken state.

The contamination tracking engine 120 may identify when items are cleaned or have otherwise transitioned from a contaminated to a decontaminated state. For example, it may be identified that the knife used to cut the raw chicken has moved to a sink and cleaning procedure has been completed on the knife (e.g., the knife has been washed) and the knife may be transitioned into a decontaminated state. The contamination tracking engine 120 may identify a state transition by matching a model for a decontamination procedure to images captured by the camera 105.

The contamination tracking engine 120 may also monitor food storage areas using sensor arrays, cameras, and other monitoring devices. The operation of the contamination tracking engine 120 in monitoring food storage areas may be similar to the operation described for preparation areas. Environmental sensors (e.g., temperature, humidity, etc.) may be placed in the food storage area. Food items in the food storage area may be identified (e.g., by a camera such as camera 105 using computer vision, etc.) and a set of rules may be selected for the food items. For example, raw chicken may be stored in a cold storage location and the set of rules for raw chicken may indicate a relative humidity range, temperature range, etc. at which raw chicken should be stored. The contamination tracking engine 120 may track items over time to determine, for example, that a raw chicken has been in a danger zone for five minutes, five hours, etc. as food contamination risk may increase as conditions of the environment and food item may change (e.g., decline, etc.) over time. The contamination tracking engine 120 may determine when the storage location violates the set of rules and may output an alert. For example, the temperature of the cold storage area may be determined to be above a temperature range for raw chicken and an alert may be displayed by the projector 110 in the preparation area.

In some examples, the contamination tracking engine 120 may track the status of multiple food items and may transmit notifications to a user indicating an order in which the food items should be prepared. For example, several ribeye steaks may be stored in a cold storage area and color differences between a first ribeye steak and a second ribeye steak may be identified in an image of the ribeye steaks and a message indicating the first ribeye steak should be cooked first may be transmitted based on the color difference.

In some examples, the contamination tracking engine 120 may receive contamination data from third-party food item purveyors (e.g., grocery store, restaurant, etc.). The contamination tracking engine 120 may recommend visiting a first third-party food item purveyor rather than a second third-party food item purveyor based on contamination history information for each of the first third-party food item purveyor and the second third-party food item purveyor contained in the contamination data. For example, the second third-party food item purveyor may have a higher number of disregarded contamination alerts than the first third-party food item purveyor.

Figure 2:
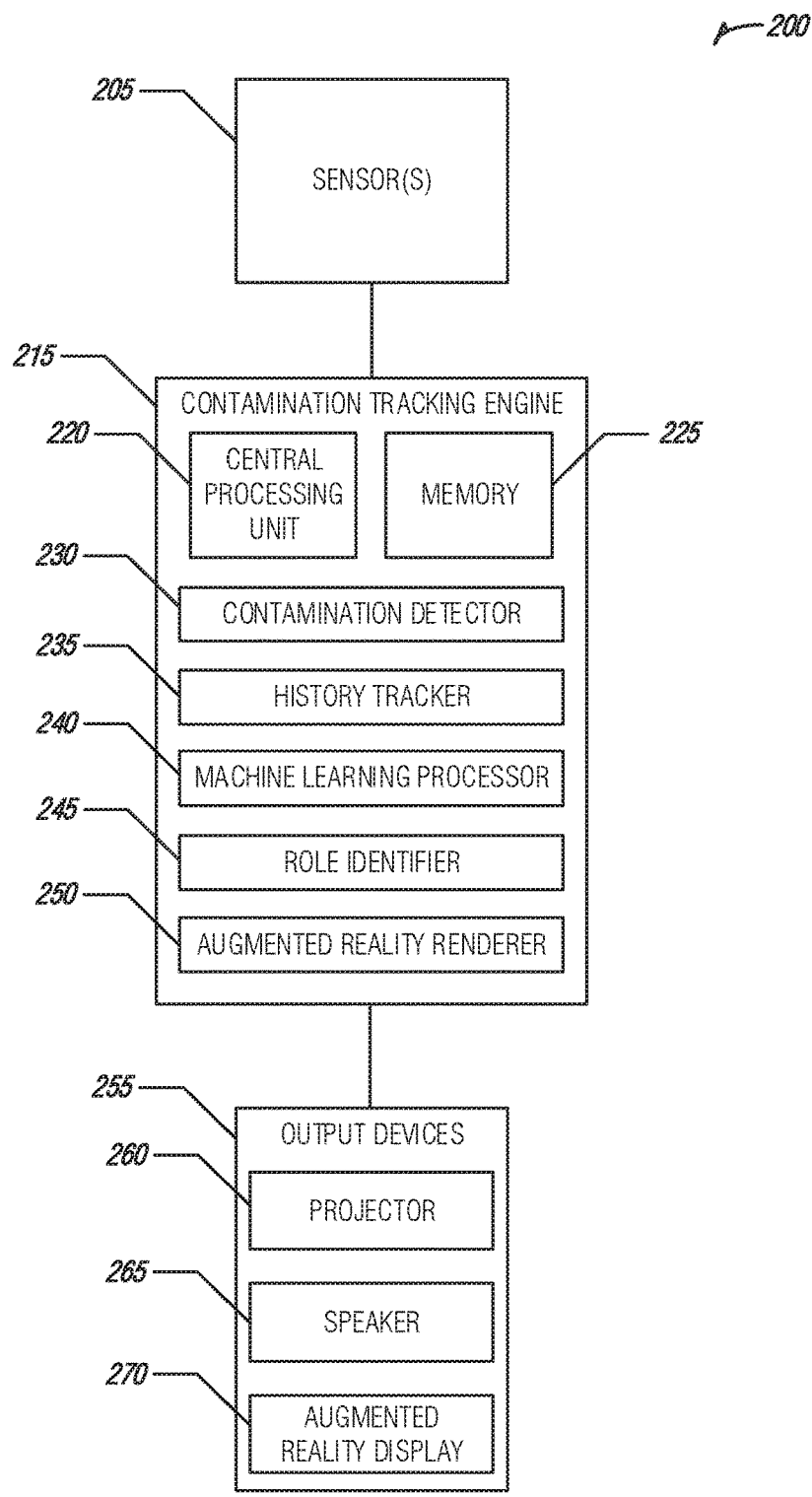
FIG. 2 illustrates a block diagram of an example of a system for computer vision and sensor assisted contamination tracking, according to an embodiment.

FIG. 2 illustrates a block diagram of an example of a system 200 for computer vision and sensor assisted contamination tracking, according to an embodiment. The system 200 may provide functionality as described in FIG. 1. The system 200 may include a variety of components such as sensor(s) 205, a contamination tracking engine 215, and output devices 255. The contamination tracking engine may include a central processing unit 220, memory 225, a contamination detector 230, a history tracker 235, a machine learning processor 240, a role identifier 245, and an augmented reality renderer 250. The output devices 255 may include a projector 260, a speaker 265, and an augmented reality display 270.

The sensor(s) 205 may include a variety of sensors including, for example, a thermometer, a bio sensor (e.g., bacteria sensor, virus sensor, mold sensor, etc.), a radiation sensor, a gas sensor, a humidity sensor, a contact sensor, etc. The sensor(s) 205 may be placed on food preparation utensils (e.g., knife, cutting board, etc.) and/or surfaces (e.g., countertop, etc.) that may come into contact with a food item and/or items that have come in contact with the food item (e.g., hands, etc.). For example, a sensor array may be embedded in a cutting board and may include a thermometer for measuring the temperature of a food item placed on the cutting board and a bacteria sensor to detect the presence of bacteria on the food item placed on the cutting board.

The sensor(s) 205 may include environmental sensors including a variety of sensors for monitoring a space in which food items area stored and/or handled. The environmental sensors may include one or more cameras (e.g., camera 105 as described in FIG. 1, RGB camera, IR camera, etc.), one or more microphones, one or more a humidity sensors, one or more thermometers, etc. For example, a thermometer and a humidity sensor may be placed in a cold storage location to monitor the temperature and humidity at which a food item is stored. In another example, an RGB camera may capture images of a food preparation area in which a food item is being prepared for cooking. In yet another example, an IR camera may be placed in the food preparation area and may measure the temperature of the food item being prepared.

The contamination tracking engine 215 may be communicatively coupled (e.g., via wireless network, wired network, shared bus, near field communication, shortwave radio signal, etc.) to the sensor(s) 205. The contamination tracking engine 215 may obtain sensor data from the sensor(s) 205. The sensor data may be processed by the central processing unit 220 using instructions stored in the memory 225 in conjunction with other components of the contamination tracking engine 215.

The contamination detector 230 may receive data from the sensor(s) 205 and may identify that a food item has moved to a monitored area using computer vision. For example, images from a camera included in the sensor(s) 205 may be obtained and processed using computer vision techniques (e.g., object recognition, etc.) to identify a raw chicken in the images. The food item may have been moved from a storage area to a food preparation area. For example, the raw chicken may have moved from cold storage to a kitchen for preparation. In some examples, the sensor(s) 205 may include cameras in the storage location and in the preparation area and computer vision techniques may be used to track the movement of the food item. For example, the raw chicken may be identified in images from the camera in the cold storage location area and may subsequently be identified in images from the camera in the kitchen.

In some examples, an image may be obtained from a camera positioned to observe the monitored area. The image may be compared to a set of imaged of food items. The set of images of food items may include an image of the food item. The food item may be selected based on the comparison and the identification that the food item has moved to the monitored area may be based on the selection. For example, the image from the camera may be compared to a set of images of food including an image of raw chicken and it may be determined that the food item in the image from the camera is raw chicken because it most closely matches the image of the raw chicken.

The contamination detector 230 may obtain sensor readings from the sensor(s) 205. For example, the raw chicken may be identified as making contact with a cutting board and a knife and may be in an observable range of an IR camera and data from sensor(s) 205 on/in the cutting board, knife, and IR camera may be obtained. In an example, the sensor readings may be obtained via a wireless network. A contamination of the food item may be determined using the sensor readings. For example, it may be determined that the raw chicken is contaminated with salmonella based on a bacteria sensor included in the sensor(s) 205. The contamination of the food item may be associated with a contamination area in the monitored area using the computer vision. For example, the contamination of the raw chicken may be associated with an area of the kitchen counter that was in contact with the raw chicken identified by the contamination tracking engine 215 using images obtained from a camera included in the sensor(s) 205.

In some examples, the contamination detector 230 may select a ruleset for the food item from a set of food specific rules sets. For example, a raw chicken ruleset may be selected for the identified raw chicken. The rulesets may include a variety of rules for handling the specific food item. For example, the ruleset for raw chicken may include rules indicating that items making contact with the raw chicken should not come in contact with cooked food items. In another example, the ruleset for raw chicken may indicate the raw chicken should be at a temperature less than 40° Fahrenheit and that being above 40° Fahrenheit for fifteen minutes indicates the raw chicken is contaminated. The sensor readings may be compared to the ruleset for the food item and the contamination may be determined based on the comparison. For example, the raw chicken may be determined to be contaminated when the temperature indicated by sensor readings from an IR camera indicates the temperature of the raw chicken has exceeded 40° Fahrenheit for fifteen minutes.

In some examples, an image of the monitored area may be obtained from a camera included in the sensor(s) 205. The contamination area may be determined for the contamination using the selected ruleset. The contamination area may be associated with a subsection of the image. For example, an image of a countertop may be obtained including the raw chicken and the rule set may indicate that a two square foot area around the raw chicken should be considered contaminated. A two square foot area of the countertop centered on the raw chicken in the image may be associated with the contamination. In some examples, the contamination detector 230 may determine that the food item is approaching contamination. For example, a person may be handling cooked beef and may be about to cut the cooked beef with a knife that previously made contact with the raw chicken (e.g., as determined by analyzing the movement of the knife using computer vision).

The contamination detector 230 may output a notification indicating the contamination (and/or potential contamination) for display in the contamination area. In some examples, the notification may be output for display on the food item. For example, a message may be generated for output that indicates the contamination and/or instructions corresponding with the contamination. In an example, the notification may be output as a projection (e.g., using the projector 260) in the contaminated area.

The contamination detector 230 may identify that a user has violated a rule for handling the food item. For example, a person handling the raw chicken may use the knife used to cut the raw chicken to cut the cooked beef despite a displayed notification indicating that the knife may only contact raw chicken. An alert may be generated for output to an output device to notify the user that a rule has been violated. For example, an alert may be output indicating that the cooked beef is contaminated. In some examples, the user may be provided with a variety of notifications. For example, a message may be displayed that the knife should only make contact with raw chicken and if the notification is ignored by moving the knife toward cooked beef an audio alert may be output (e.g., by the speaker 265) that intensifies as the distance between the knife and the cooked beef diminishes.

In some examples, a first action performed may be identified in response to a notification. For example, the notification may indicate that the knife should be washed and it may be identified that a person using the knife is moving it to the cooked beef. The first action performed may be compared with an action model for the notification. In an example, the action model may include decontamination procedures for a contaminated item. For example, the knife, contaminated by raw chicken, may correspond with an action model for decontaminating the knife by washing and moving the knife toward the cooked beef may be compared with the model. A message may be transmitted indicating a second action to be performed based on the comparison. For example, the message may include taking the knife to the sink to be washed rather than using the knife to cut the cooked beef.

The contamination detector 230 may determine when items have been decontaminated. For example, a knife used to cut the raw chicken may have been washed. The contamination detector 230 may discontinue tracking the decontaminated item until the item is again detected as contaminated. For example, the washed knife may not be tracked until it has been identified making contact with another food item.

In some examples, it may be identified that the food item is nearing the contamination using the sensor(s) 205 and a message may be transmitted including instructions for avoiding the contamination. For example, it may be detected that the cooked beef has been removed from a contact sensor in a pan and is touching a contact sensor in a cutting board on an area of a countertop contaminated by the raw chicken and a grid may be displayed indicating the contaminated area and a decontaminated area with instructions to place the cooked beef on a cutting board in the decontaminated area. In some examples, an image of the food item may be captured using a camera. It may be identified that the food item is nearing the contamination using the image of the food and a message may be transmitted including instructions for avoiding the contamination. For example, the image may indicate that the cooked beef has moved from the pan to the cutting board and the message indicating that the cooked beef should be moved to a cutting board in the decontaminated space may be displayed.

In some examples, the contamination detector 230 may monitor food storage locations for contamination. A storage area of the food item may be identified. For example, the raw chicken may be stored in a walk-in refrigerator. A set of environmental sensor measurements may be obtained (e.g., from the sensor(s) 205) for the storage area. It may be determined that the food item is in a pre-contaminated state using the set of environmental sensor measurements. For example, the walk-in refrigerator may have a temperature higher than indicated by a rule in the ruleset for raw chicken. A message may be transmitted including instructions for removing the food item from the pre-contaminated state. For example, a message may be projected on the door of the walk-in refrigerator indicating that the temperature should be lowered. In some examples, a message may be transmitted to a component (e.g., cooling unit, heating element, humidifier, dehumidifier, etc.) of the storage area to automatically adjust a condition (e.g., temperature, humidity level, etc.) of the storage area.

The history tracker 235 may collect and maintain a history of contamination and/or ignored notifications. For example, the history tracker 235 may store details (e.g., date, time, notification text, person present, etc.) about the knife previously used to cut raw chicken making contact with cooked beef. The history tracker 235 may generate output including the history for display on a display device. The history may be useful in tracking foodborne illness outbreaks, compliance violations, etc. The history tracker 235 may generate output for use by the machine learning processor 240.

The machine learning processor 240 may use a variety of machine learning techniques including, but not limited to, naïve Bayes, linear regression, logistic regression, decision trees, deep learning, k-means, etc. The machine learning processor 240 may use outputs from the history tracker 235, contamination detector 230, and sensor(s) 205 to make adjustments to and/or create new rules for including in the food specific rulesets. For example, a person may ignore a notification about the raw chicken nearing contamination because the raw chicken is approaching 40° Fahrenheit (e.g., by not returning the raw chicken to a cold storage area, etc.) and the inaction may be used as input, along with other instances of inaction, by the machine learning processor 240 to adjust the rule set for the raw chicken to avoid notification that the raw chicken is nearing 40° Fahrenheit. This may prevent unnecessary notification in situations where chicken is routinely cooked as it approaches 40° Fahrenheit.

The role identifier 245 may identify a role of a person identified by the contamination tracking engine 215 (e.g., identified in an image captured by a camera included in the sensor(s) 205, etc.). For example, a person handling the raw chicken may be identified and a role of chef may be identified for the person handling the raw chicken. In some examples, the role may correspond to a user profile maintained by the contamination tracking engine. For example, the person handling the raw chicken may be identified as corresponding with a user profile for "Bob." The role may be used in the selection of a ruleset for the food item. In some examples, the role may include custom rules that may supplement and/or modify the ruleset for the food item. For example, Bob's profile may include a rule indicating that a knife used for cutting raw chicken must be washed before contacting another food item and an alert may be generated for display when the knife is determined to have moved away from the raw chicken indicating the knife must be washed.

In some examples, the role may indicate an allergy of a person identified in a food serving area and the ruleset may be supplemented and/or modified based on the allergy. For example, "Tina" may be identified in a restaurant and her profile may indicate she is allergic to peanuts and a rule indicating that a food item prepared for Tina must not make contact with peanuts or surfaces and/or items contaminated with peanuts. The activities of an identified person corresponding to a role may be tracked and may be used as input to the machine learning processor 240 to make adjustments to role-based rules. For example, Tina may remove tomatoes from her sandwich and the removal of the tomatoes (and past removal of tomatoes) may be used as input to generate output indicating that food items prepared for Tina should not include tomatoes.

The augmented reality renderer 250 may render output for display by an augmented reality display 270. For example, contaminated areas of an image of the food preparation area may be rendered on a live video stream displayed in a virtual reality headset. In an example, the contaminated areas of the food preparation area may be mapped in a three-dimensional coordinate system and plotted in the video display of the augmented reality display 270. For example, a grid may be displayed on the screen in the augmented reality headset indicating contaminated areas and no contaminated areas. In some examples, output from the contamination tracking engine 215 may be rendered for display in smart glasses. For example, a person handling the raw chicken may be wearing smart glasses and notifications, alerts, and areas of contamination may be displayed using the smart glasses providing the user with real-time information regarding contamination in the food preparation area.

The output devices 255 may include a variety of device used to present information to a user. The output devices may include the projector 260, the speaker 265, and the augmented reality display 270. The projector 260 may project data (e.g., text, images, etc.). The projector 260 may receive output from the contamination tracking engine 215 and may display the information by projecting it on a surface. The projector 260 may be positioned such that it may display information throughout the area containing the food item. In an example, information may be displayed beside the food item. In another example, the information may be displayed on the food item. The speaker 265 may receive output from the contamination tracking engine 215 and may present audio data (e.g., tones, voice guidance, etc.) in the area containing the food item. For example, the speaker 265 may present an audio tone if a notification displayed by the projector 260 is ignored. The augmented reality display 270 may receive output from the contamination tracking engine 215 and may display information to a user. The augment reality display 270 may be in a variety of forms, for example, a virtual reality headset, smart glasses, projected overlays, etc.

The present subject matter may be implemented in various configurations. For example, the contamination detector 230, the history tracker 235, the machine learning processor 240, the role identifier 245, and the augmented reality renderer 250 may be implemented in different (or the same) computing systems (e.g., a single server, a collection of servers, a cloud-based computing platform, etc.). A computing system may comprise one or more processors (e.g., hardware processor 502 described in FIG. 5, etc.) that execute software instructions, such as those used to define a software or computer program, stored in a computer-readable storage medium such as a memory device (e.g., a main memory 504 and a static memory 506 as described in FIG. 5, a Flash memory, random access memory (RAM), or any other type of volatile or non-volatile memory that stores instructions), or a storage device (e.g., a disk drive, or an optical drive). Alternatively or additionally, the computing system may comprise dedicated hardware, such as one or more integrated circuits, one or more Application Specific Integrated Circuits (ASICs), one or more Application Specific Special Processors (ASSPs), one or more Field Programmable Gate Arrays (FPGAs), or any combination of the foregoing examples of dedicated hardware, for performing the techniques described in this disclosure.

Figure 3:
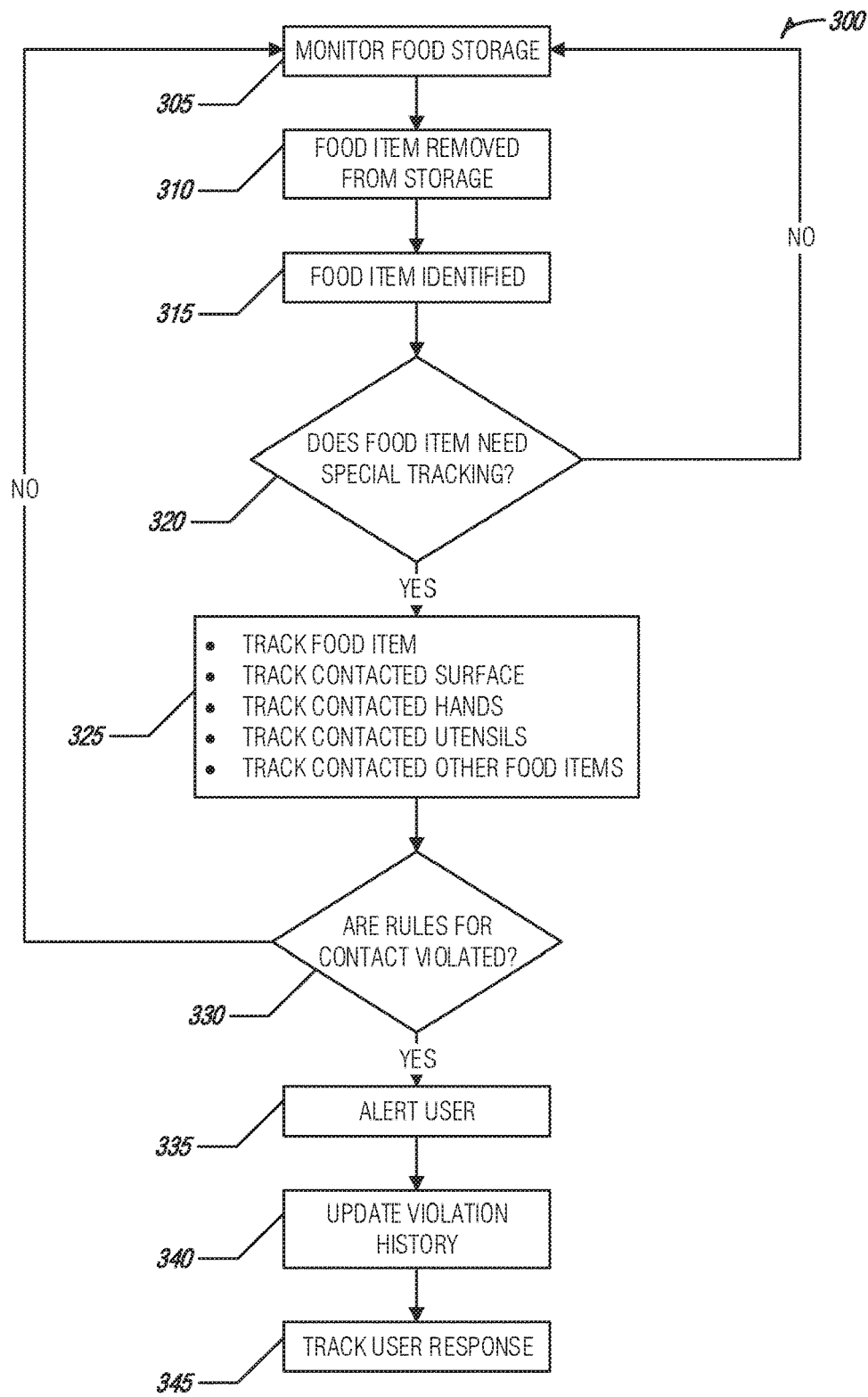
FIG. 3 illustrates a flow diagram of an example of a process for computer vision and sensor assisted contamination tracking, according to an embodiment.

FIG. 3 illustrates a flow diagram of an example of a process 300 for computer vision and sensor assisted contamination tracking, according to an embodiment. The process 300 may provide functionality as described in FIGS. 1 and 2.

At operation 305, food storage may be monitored. Environmental sensors (e.g., sensor(s) 205 as described in FIG. 2, etc.) may be placed in the food storage item and may monitor the conditions of the food storage location and movement of food items located in the food storage location. For example, a thermometer, a humidity sensor, and a camera may be positioned in the food storage location to monitor the temperature and humidity of the food storage location and images from the camera may be analyzed using computer vision techniques to track movement of stored food items.

At operation 310, it may be determined (e.g., using a camera and computer vision, etc.) that a food item has moved from storage. For example, a camera in the food storage location and/or a camera in a food preparation area may output images that may be analyzed using computer vision techniques to determine that the food item has been removed from the food storage location.

At operation 315, the food item may be identified. For example, the images from the camera in the food storage location and/or the food preparation area may be analyzed using computer vision techniques to identify the food item in the images.

At decision 320, it may be determined if the food item needs special tracking. Some food items like raw meat and known allergens may have special handling rules indicating that the food item should be tracked while other food items such as dried grains may not have special handling instructions indicating that the food item should not be tracked. A set of food specific rulesets may be accessed to determine if the food item should be tracked. If a ruleset matches the food item, the food item may be tracked using the matching ruleset. If a matching ruleset is not found, the process 300 returns to operation 305 and the food storage location is monitored.

At operation 325, the ruleset of the food item is used to track the food item, and food item contacted surfaces, hands, utensils, and other food items. The special handling of food items may include preventing the food item from making contact with other items as the food item may be a contaminate (e.g., raw chicken may carry salmonella, etc.). Thus, the food item and any items making contact with the food item may be tracked to identify areas of contamination.

At decision 330, it may be determined if rules for contact are violated. The ruleset for the food item may indicate that the food item (or items contacting the food item) should not contact other items. For example, a knife used to cut raw chicken should not be used to cut cooked beef, etc. The movement of an item making contact with the food item (e.g., a knife, cutting board, hands, etc.) may be tracked using images from a camera using computer vision analysis. If it is determined that a rule has been violated (e.g., a knife used to cut raw chicken is used to cut cooked beef, etc.) the process continues to operation 335. If rules for contact are not violated, the process 300 continues to monitor the food storage at operation 305. In some examples, it may be determined that an item has been decontaminated and should no longer be tracked and the process 300 may continue to operation 305. For example, it may be determined that the knife used to cut raw chicken has been washed and a different ruleset (e.g., a ruleset for decontaminated items, etc.) may be selected for the knife because it has been decontaminated.

At operation 335, having determined at decision 330 that contact rules have been violated, an alert may be transmitted to a user. The user may be a person handling the food item, a person supervising, the handling of the food item, etc. The alert may be in a variety of formats including, but not limited to, a projection of text and/or images near the violation, audio queues, augmented reality display, etc. The alert provides an indication to the user that a rule has been violated and an item has become contaminated.

At operation 340, a violation history may be updated. A history of violation may be maintained including information about violations of rules in the food item specific rulesets. For example, the violation history may include each time a knife used to cut raw chicken is used to cut a cooked food item. The current violation may be appended or otherwise added to the violation history. Thus, a record of violations may be referenced in the event of a foodborne illness outbreak, inspection, etc.

At operation 345, the user's response may be tracked. It may be determined (e.g., using computer vision, etc.) how the user responded to the alert provided at operation 335. For example, the user cutting the cooked beef with the knife previously used to cut the raw chicken may dispose of the cooked beef, ignore the alert and continue cutting the cooked beef with the contaminated knife, or perform another action. In some examples, the user's response may be used as machine learning input (e.g., by machine learning processor 240 as described in FIG. 2, etc.) to make adjustments to rulesets and/or user preferences. For example, the user may wash the knife used to cut the raw chicken in a cleaning solution before cutting the cooked beef and the ruleset may be adjusted to indicate that the user's activity of washing the knife before cutting the cooked beef does not violate a contact rule (e.g., because the knife has been decontaminated).

Figure 4:
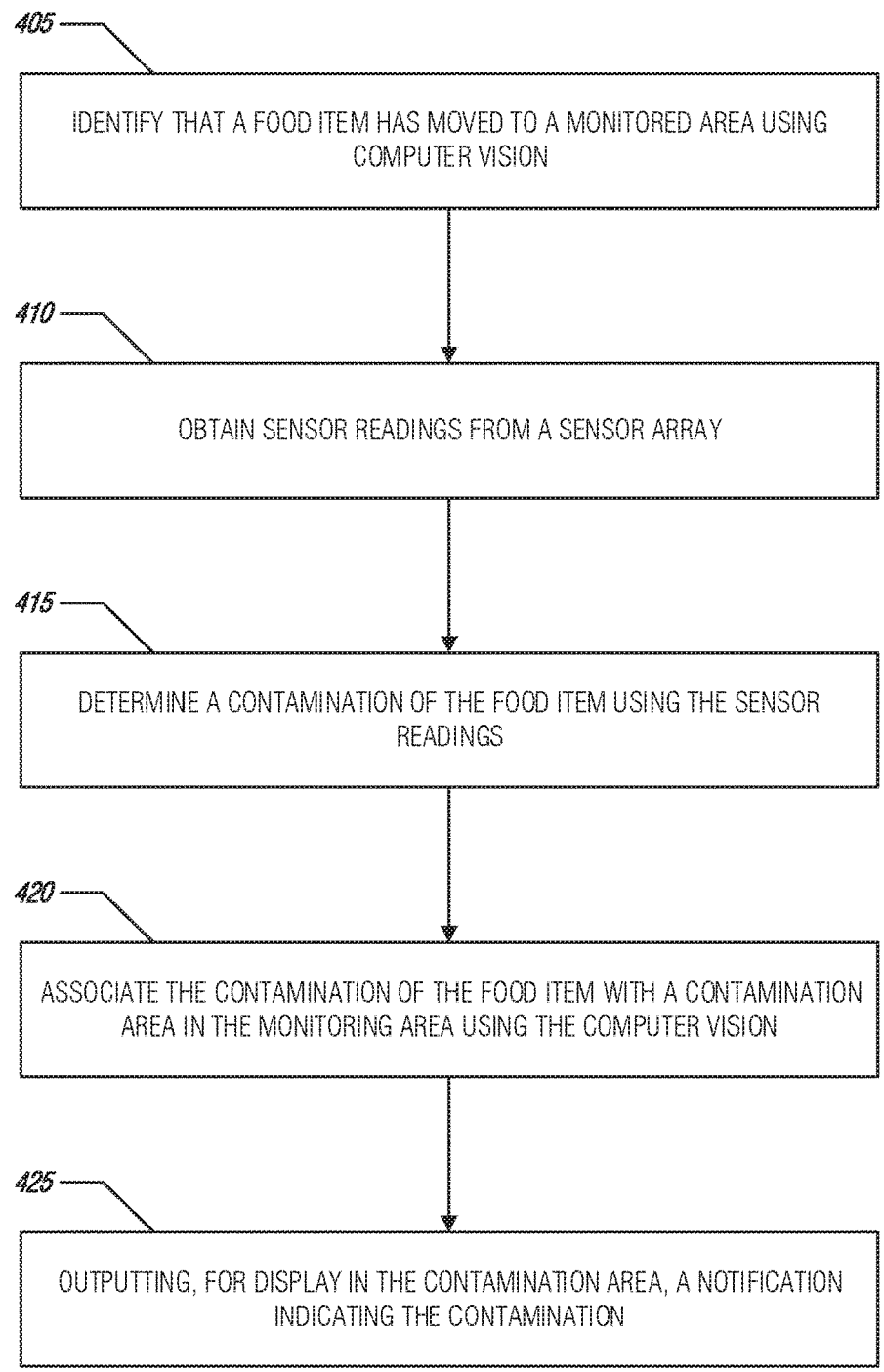
FIG. 4 illustrates an example of a method for computer vision and sensor assisted contamination tracking, according to an embodiment.

FIG. 4 illustrates an example of a method 400 for computer vision and sensor assisted contamination tracking, according to an embodiment. The method 400 may provide functionality as described in FIGS. 1 and 2.

At operation 405, it may be identified that a food item has moved to a monitored area using computer vision. In an example, an image may be obtained from a camera positioned to observe the monitored area. The image may be compared to a set of images of food items. The set of images of food items may include an image of the food item. The food item may be selected based on the comparison and it may be identified that the food item has moved to the monitored area based on the selection.

At operation 410, sensor readings may be obtained from a sensor array. In an example, the sensor readings may be obtained via a wireless network. In an example, the sensor array may include a thermometer. In an example, the sensor array may include a humidity sensor. In an example, the sensor array may include a bacteria sensor. In an example, the sensor array may include a gas sensor. In an example, the sensor array may include an infrared camera. In an example, the sensor array may include a radiation sensor. In an example, the sensor array may include a contact sensor.

At operation 415, a contamination of the food item may be determined using the sensor readings. In an example, a ruleset for the food item may be selected from a set of food specific rulesets. The sensor readings may be compared to the ruleset for the food item and the contamination may be determined based on the comparison.

At operation 420, the contamination of the food item may be associated with a contamination area in the monitored area using the computer vision. In an example, an image of the monitored area may be obtained from a camera. The contamination area for the contamination may be determined using the selected ruleset and the contamination area may be associated with a subsection of the image.

At operation 425, a notification may be output for display in the contamination area indicating the contamination. In an example, the notification may be output as a projection in the contaminated area. In some examples, a first action performed in response to the notification may be identified. The first action performed may be compared with an action model for the notification and a message may be transmitted indicating a second action to be performed based on the comparison.

In some examples, it may be identified that the food item is nearing the contamination using the sensor array and a message may be transmitted including instructions for avoiding the contamination. In some examples, an image of the food item may be captured using a camera. It may be identified that the food item is nearing the contamination using the image of the food item and a message may be transmitted including instructions for avoiding the contamination.

In some examples, a storage area of the food item may be identified. A set of environmental sensor measurements may be obtained. It may be determined that the food item is in a pre-contaminated state using the set of environmental sensor measurements and a message may be transmitted including instructions for removing the food item from the pre-contaminated state.

Figure 5:
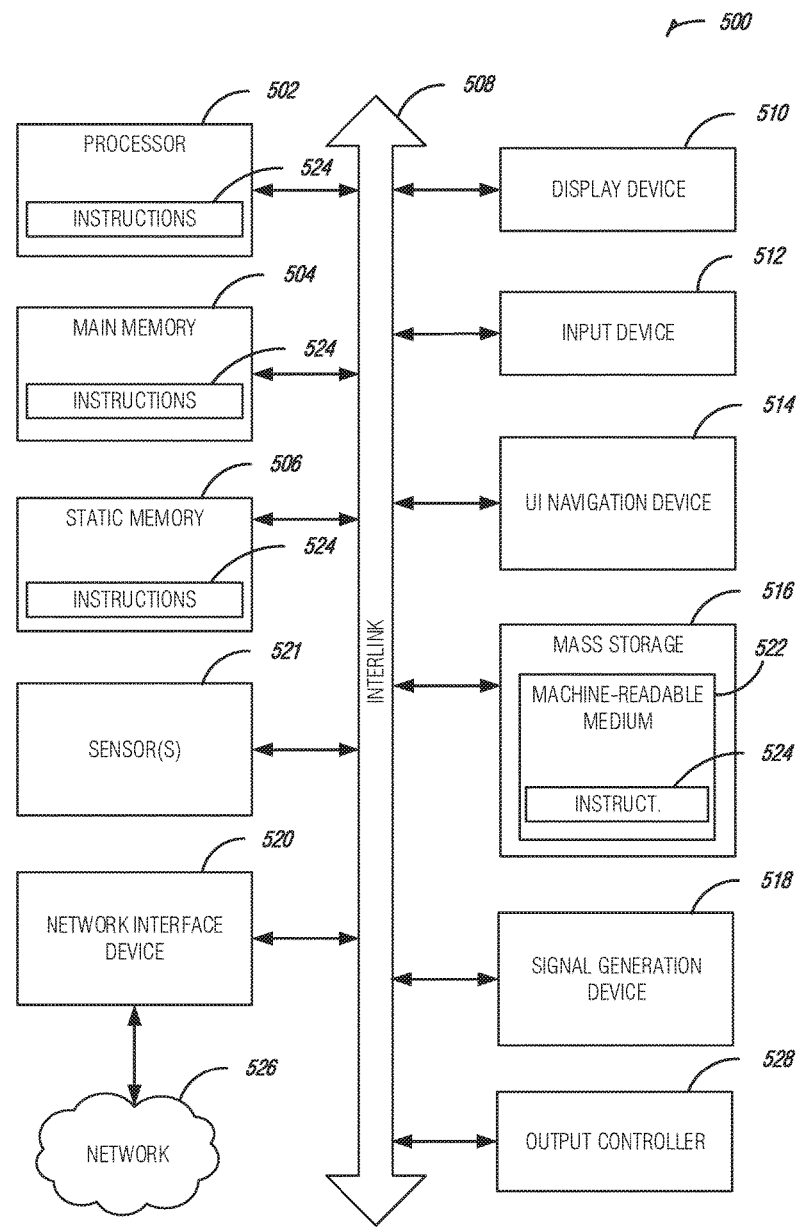
FIG. 5 is a block diagram illustrating an example of a machine upon which one or more embodiments may be implemented.

FIG. 5 illustrates a block diagram of an example machine 500 upon which any one or more of the techniques (e.g., methodologies) discussed herein may perform. In alternative embodiments, the machine 500 may operate as a standalone device or may be connected (e.g., networked) to other machines. In a networked deployment, the machine 500 may operate in the capacity of a server machine, a client machine, or both in server-client network environments. In an example, the machine 500 may act as a peer machine in peer-to-peer (P2P) (or other distributed) network environment. The machine 500 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 500 may include a hardware processor 502 (e.g., a central processing unit (CPU), a graphics processing unit (GPU), a hardware processor core, or any combination thereof), a main memory 504 and a static memory 506, some or all of which may communicate with each other via an interlink (e.g., bus) 508. The machine 500 may further include a display unit 510, an alphanumeric input device 512 (e.g., a keyboard), and a user interface (UI) navigation device 514 (e.g., a mouse). In an example, the display unit 510, input device 512 and UI navigation device 514 may be a touch screen display. The machine 500 may additionally include a storage device (e.g., drive unit) 516, a signal generation device 518 (e.g., a speaker), a network interface device 520, and one or more sensors 521, such as a global positioning system (GPS) sensor, compass, accelerometer, or other sensor. The machine 500 may include an output controller 528, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 516 may include a machine readable medium 522 on which is stored one or more sets of data structures or instructions 524 (e.g., software) embodying or utilized by any one or more of the techniques or functions described herein. The instructions 524 may also reside, completely or at least partially, within the main memory 504, within static memory 506, or within the hardware processor 502 during execution thereof by the machine 500. In an example, one or any combination of the hardware processor 502, the main memory 504, the static memory 506, or the storage device 516 may constitute machine readable media.

While the machine readable medium 522 is illustrated as a single medium, the term "machine readable medium" may include a single medium or multiple media (e.g., a centralized or distributed database, and/or associated caches and servers) configured to store the one or more instructions 524.

The term "machine readable medium" may include any medium that is capable of storing, encoding, or carrying instructions for execution by the machine 500 and that cause the machine 500 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 524 may further be transmitted or received over a communications network 526 using a transmission medium via the network interface device 520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 520 may include one or more physical jacks (e.g., Ethernet, coaxial, or phone jacks) or one or more antennas to connect to the communications network 526. In an example, the network interface device 520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 500, and includes digital or analog communications signals or other intangible medium to facilitate communication of such software.

ADDITIONAL NOTES & EXAMPLES

Example 1 is a system for tracking food contamination using computer vision and a sensor array, the system comprising: at least one processor; a memory including instructions that, when executed by the at least one processor, cause the at least one processor to: identify that a food item has moved to a monitored area using the computer vision; obtain sensor readings from the sensor array; determine a potential contamination of the food item using the sensor readings; associate the potential contamination of the food item with a contamination area in the monitoring area using the computer vision; and; output, for display in the contamination area, a notification indicating the potential contamination.

In Example 2, the subject matter of Example 1 optionally includes the instructions to identify that the food item has moved into the monitored area using computer further comprising instructions to: obtain an image from a camera positioned to observe the monitored area; compare the image to a set of images of food items, the set of images of food items including an image of the food item; select the food item based on the comparison; and identify that the food item has moved to the monitored area based on the selection.

In Example 3, the subject matter of any one or more of Examples 1-2 optionally include instructions to: select a ruleset for the food item from a set of food specific rulesets; compare the sensor readings to the ruleset for the food item; and determine the potential contamination based on the comparison.

In Example 4, the subject matter of Example 3 optionally includes instructions to: obtain an image of the monitored area from a camera; determine the contamination area for the potential contamination using the selected ruleset; and associate the contamination area with a subsection of the image.

In Example 5, the subject matter of any one or more of Examples 3-4 optionally include instructions to: identify an action of a person handling the food item using the computer vision and the sensor readings; determine that the action violates a rule of the ruleset for the food item; and modify the rule by processing the violation of the rule using machine learning.

In Example 6, the subject matter of any one or more of Examples 3-5 optionally include wherein the instructions to select a ruleset for the food item from a set of food specific rulesets comprises instructions to: identify a person handling the food item using the computer vision; determine a user profile for the person handling the food item; and select the ruleset in part based on the user profile.

In Example 7, the subject matter of any one or more of Examples 3-6 optionally include wherein the instructions to select a ruleset for the food item from a set of food specific rulesets comprises instructions to: identify a person for whom the food item is being prepared using the computer vision; determine a user profile for the person for whom the food item is being prepared; and select the ruleset in part based on the user profile.

In Example 8, the subject matter of any one or more of Examples 3-7 optionally include instructions to: identify that an object has contacted the food item using the computer vision and the sensor readings; associate the potential contamination with the object; determine that the object has made contact with a another food item in violation of a rule of the ruleset for the food item; store an indication of the violation of the rule; and output a message indicating the violation to a surface near the object.

In Example 9, the subject matter of any one or more of Examples 3-8 optionally include instructions to: select a food temperature rule from the ruleset for the food item; determine the temperature of the food item over a time period using the sensor readings; calculate a rate of temperature change for the food item over the time period; calculate a contamination time for the food item using the rate of temperature change for the food item; and transmit, for display in the contamination area, a message including the contamination time for the food item.

In Example 10, the subject matter of any one or more of Examples 1-9 optionally include instructions to: identify a first action performed in response to the notification; compare the first action performed with an action model for the notification; and transmit a message indicating a second action to be performed based on the comparison.

In Example 11, the subject matter of any one or more of Examples 1-10 optionally include instructions to: identify that the food item is nearing the potential contamination using the sensor array; and transmit a message including instructions for avoiding the potential contamination.

In Example 12, the subject matter of any one or more of Examples 1-11 optionally include instructions to: capture an image of the food item using a camera; identify the food item is nearing the potential contamination using the image of the food item; and transmit a message including instructions for avoiding the potential contamination.

In Example 13, the subject matter of any one or more of Examples 1-12 optionally include instructions to: identify a storage area of the food item; obtain a set of environmental sensor measurements for the storage area; determine that the food item is in a pre-contaminated state using the set of environmental sensor measurements; and transmit a message including instructions for removing the food item from the pre-contaminated state.

In Example 14, the subject matter of any one or more of Examples 1-13 optionally include wherein the notification is output as a projection in the contaminated area.

In Example 15, the subject matter of any one or more of Examples 1-14 optionally include wherein the sensor readings are obtained via a wireless network.

In Example 16, the subject matter of any one or more of Examples 1-15 optionally include wherein the instructions to obtain sensor readings from the sensor array comprises instructions to: obtain a food surface temperature from a thermometer in the sensor array.

In Example 17, the subject matter of any one or more of Examples 1-16 optionally include wherein the instructions to obtain sensor readings from the sensor array comprises instructions to: obtain an environmental relative humidity from humidity sensor in the sensor array.

In Example 18, the subject matter of any one or more of Examples 1-17 optionally include wherein the instructions to obtain sensor readings from the sensor array comprises instructions to: obtain a food bacteria count from a bacteria sensor in the sensor array.

In Example 19, the subject matter of any one or more of Examples 1-18 optionally include wherein the instructions to obtain sensor readings from the sensor array comprises instructions to: obtain a food gas measurement from a gas sensor in the sensor array.

In Example 20, the subject matter of any one or more of Examples 1-19 optionally include wherein the instructions to obtain sensor readings from the sensor array comprises instructions to: obtain a food surface temperature from an infrared camera in the sensor array.

In Example 21, the subject matter of any one or more of Examples 1-20 optionally include wherein the instructions to obtain sensor readings from the sensor array comprises instructions to: obtain a food radiation count from a radiation sensor in the sensor array.

In Example 22, the subject matter of any one or more of Examples 1-21 optionally include wherein the instructions to obtain sensor readings from the sensor array comprises instructions to: obtain an indication of food contact from a contact sensor in the sensor array.

Example 23 is at least one machine readable medium including instructions for tracking food contamination using computer vision and a sensor array that, when executed by a machine, cause the machine to: identify that a food item has moved to a monitored area using the computer vision; obtain sensor readings from the sensor array; determine a potential contamination of the food item using the sensor readings; associate the potential contamination of the food item with a contamination area in the monitoring area using the computer vision; and; output, for display in the contamination area, a notification indicating the potential contamination.

In Example 24, the subject matter of Example 23 optionally includes the instructions to identify that the food item has moved into the monitored area using computer further comprising instructions to: obtain an image from a camera positioned to observe the monitored area; compare the image to a set of images of food items, the set of images of food items including an image of the food item; select the food item based on the comparison; and identify that the food item has moved to the monitored area based on the selection.

In Example 25, the subject matter of any one or more of Examples 23-24 optionally include instructions to: select a ruleset for the food item from a set of food specific rulesets; compare the sensor readings to the ruleset for the food item; and determine the potential contamination based on the comparison.

In Example 26, the subject matter of Example 25 optionally includes instructions to: obtain an image of the monitored area from a camera; determine the contamination area for the potential contamination using the selected ruleset; and associate the contamination area with a subsection of the image.

In Example 27, the subject matter of any one or more of Examples 25-26 optionally include instructions to: identify an action of a person handling the food item using the computer vision and the sensor readings; determine that the action violates a rule of the ruleset for the food item; and modify the rule by processing the violation of the rule using machine learning.

In Example 28, the subject matter of any one or more of Examples 25-27 optionally include wherein the instructions to select a ruleset for the food item from a set of food specific rulesets comprises instructions to: identify a person handling the food item using the computer vision; determine a user profile for the person handling the food item; and select the ruleset in part based on the user profile.

In Example 29, the subject matter of any one or more of Examples 25-28 optionally include wherein the instructions to select a ruleset for the food item from a set of food specific rulesets comprises instructions to: identify a person for whom the food item is being prepared using the computer vision; determine a user profile for the person for whom the food item is being prepared; and select the ruleset in part based on the user profile.

In Example 30, the subject matter of any one or more of Examples 25-29 optionally include instructions to: identify that an object has contacted the food item using the computer vision and the sensor readings; associate the potential contamination with the object; determine that the object has made contact with a another food item in violation of a rule of the ruleset for the food item; store an indication of the violation of the rule; and output a message indicating the violation to a surface near the object.

In Example 31, the subject matter of any one or more of Examples 25-30 optionally include instructions to: select a food temperature rule from the ruleset for the food item; determine the temperature of the food item over a time period using the sensor readings; calculate a rate of temperature change for the food item over the time period; calculate a contamination time for the food item using the rate of temperature change for the food item; and transmit, for display in the contamination area, a message including the contamination time for the food item.

In Example 32, the subject matter of any one or more of Examples 23-31 optionally include instructions to: identify a first action performed in response to the notification; compare the first action performed with an action model for the notification; and transmit a message indicating a second action to be performed based on the comparison.

In Example 33, the subject matter of any one or more of Examples 23-32 optionally include instructions to: identify that the food item is nearing the potential contamination using the sensor array; and transmit a message including instructions for avoiding the potential contamination.

In Example 34, the subject matter of any one or more of Examples 23-33 optionally include instructions to: capture an image of the food item using a camera; identify the food item is nearing the potential contamination using the image of the food item; and transmit a message including instructions for avoiding the potential contamination.

In Example 35, the subject matter of any one or more of Examples 23-34 optionally include instructions to: identify a storage area of the food item; obtain a set of environmental sensor measurements for the storage area; determine that the food item is in a pre-contaminated state using the set of environmental sensor measurements; and transmit a message including instructions for removing the food item from the pre-contaminated state.

In Example 36, the subject matter of any one or more of Examples 23-35 optionally include wherein the notification is output as a projection in the contaminated area.

In Example 37, the subject matter of any one or more of Examples 23-36 optionally include wherein the sensor readings are obtained via a wireless network.

In Example 38, the subject matter of any one or more of Examples 23-37 optionally include wherein the instructions to obtain sensor readings from the sensor array comprises instructions to: obtain a food surface temperature from a thermometer in the sensor array.

In Example 39, the subject matter of any one or more of Examples 23-38 optionally include wherein the instructions to obtain sensor readings from the sensor array comprises instructions to: obtain an environmental relative humidity from humidity sensor in the sensor array.

In Example 40, the subject matter of any one or more of Examples 23-39 optionally include wherein the instructions to obtain sensor readings from the sensor array comprises instructions to: obtain a food bacteria count from a bacteria sensor in the sensor array.

In Example 41, the subject matter of any one or more of Examples 23-40 optionally include wherein the instructions to obtain sensor readings from the sensor array comprises instructions to: obtain a food gas measurement from a gas sensor in the sensor array.

In Example 42, the subject matter of any one or more of Examples 23-41 optionally include wherein the instructions to obtain sensor readings from the sensor array comprises instructions to: obtain a food surface temperature from an infrared camera in the sensor array.

In Example 43, the subject matter of any one or more of Examples 23-42 optionally include wherein the instructions to obtain sensor readings from the sensor array comprises instructions to: obtain a food radiation count from a radiation sensor in the sensor array.

In Example 44, the subject matter of any one or more of Examples 23-43 optionally include wherein the instructions to obtain sensor readings from the sensor array comprises instructions to: obtain an indication of food contact from a contact sensor in the sensor array.

Example 45 is a method for tracking food contamination using computer vision and a sensor array, the method comprising: identifying that a food item has moved to a monitored area using the computer vision; obtaining sensor readings from the sensor array; determining a potential contamination of the food item using the sensor readings; associating the potential contamination of the food item with a contamination area in the monitoring area using the computer vision; and; outputting, for display in the contamination area, a notification indicating the potential contamination.

In Example 46, the subject matter of Example 45 optionally includes the identifying that the food item has moved into the monitored area using computer further comprising: obtaining an image from a camera positioned to observe the monitored area; comparing the image to a set of images of food items, the set of images of food items including an image of the food item; selecting the food item based on the comparison; and identifying that the food item has moved to the monitored area based on the selection.

In Example 47, the subject matter of any one or more of Examples 45-46 optionally include selecting a ruleset for the food item from a set of food specific rulesets; comparing the sensor readings to the ruleset for the food item; and determining the potential contamination based on the comparison.

In Example 48, the subject matter of Example 47 optionally includes obtaining an image of the monitored area from a camera; determining the contamination area for the potential contamination using the selected ruleset; and associating the contamination area with a subsection of the image.

In Example 49, the subject matter of any one or more of Examples 47-48 optionally include identifying an action of a person handling the food item using the computer vision and the sensor readings; determining that the action violates a rule of the ruleset for the food item; and modifying the rule by processing the violation of the rule using machine learning.

In Example 50, the subject matter of any one or more of Examples 47-49 optionally include wherein selecting a ruleset for the food item from a set of food specific rulesets comprises: identifying a person handling the food item using the computer vision; determining a user profile for the person handling the food item; and selecting the ruleset in part based on the user profile.

In Example 51, the subject matter of any one or more of Examples 47-50 optionally include wherein selecting a ruleset for the food item from a set of food specific rulesets comprises: identifying a person for whom the food item is being prepared using the computer vision; determining a user profile for the person for whom the food item is being prepared; and selecting the ruleset in part based on the user profile.

In Example 52, the subject matter of any one or more of Examples 47-51 optionally include identifying that an object has contacted the food item using the computer vision and the sensor readings; associating the potential contamination with the object; determining that the object has made contact with a another food item in violation of a rule of the ruleset for the food item; storing an indication of the violation of the rule; and outputting a message indicating the violation to a surface near the object.

In Example 53, the subject matter of any one or more of Examples 47-52 optionally include selecting a food temperature rule from the ruleset for the food item; determining the temperature of the food item over a time period using the sensor readings; calculating a rate of temperature change for the food item over the time period; calculating a contamination time for the food item using the rate of temperature change for the food item; and transmitting, for display in the contamination area, a message including the contamination time for the food item.

In Example 54, the subject matter of any one or more of Examples 45-53 optionally include identifying a first action performed in response to the notification; comparing the first action performed with an action model for the notification; and transmitting a message indicating a second action to be performed based on the comparison.

In Example 55, the subject matter of any one or more of Examples 45-54 optionally include identifying that the food item is nearing the potential contamination using the sensor array; and transmitting a message including instructions for avoiding the potential contamination.

In Example 56, the subject matter of any one or more of Examples 45-55 optionally include capturing an image of the food item using a camera; identifying the food item is nearing the potential contamination using the image of the food item; and transmitting a message including instructions for avoiding the potential contamination.

In Example 57, the subject matter of any one or more of Examples 45-56 optionally include identifying a storage area of the food item; obtaining a set of environmental sensor measurements for the storage area; determining that the food item is in a pre-contaminated state using the set of environmental sensor measurements; and transmitting a message including instructions for removing the food item from the pre-contaminated state.

In Example 58, the subject matter of any one or more of Examples 45-57 optionally include wherein the notification is output as a projection in the contaminated area.

In Example 59, the subject matter of any one or more of Examples 45-58 optionally include wherein the sensor readings are obtained via a wireless network.

In Example 60, the subject matter of any one or more of Examples 45-59 optionally include wherein obtaining sensor readings from the sensor array comprises: obtaining a food surface temperature from a thermometer in the sensor array.

In Example 61, the subject matter of any one or more of Examples 45-60 optionally include wherein obtaining sensor readings from the sensor array comprises: obtaining an environmental relative humidity from humidity sensor in the sensor array.

In Example 62, the subject matter of any one or more of Examples 45-61 optionally include wherein obtaining sensor readings from the sensor array comprises: obtaining a food bacteria count from a bacteria sensor in the sensor array.

In Example 63, the subject matter of any one or more of Examples 45-62 optionally include wherein obtaining sensor readings from the sensor array comprises: obtaining a food gas measurement from a gas sensor in the sensor array.

In Example 64, the subject matter of any one or more of Examples 45-63 optionally include wherein obtaining sensor readings from the sensor array comprises: obtaining a food surface temperature from an infrared camera in the sensor array.

In Example 65, the subject matter of any one or more of Examples 45-64 optionally include wherein obtaining sensor readings from the sensor array comprises: obtaining a food radiation count from a radiation sensor in the sensor array.

In Example 66, the subject matter of any one or more of Examples 45-65 optionally include wherein obtaining sensor readings from the sensor array comprises: obtaining an indication of food contact from a contact sensor in the sensor array.

Example 67 is a system to implement tracking food contamination using computer vision and a sensor array, the system comprising means to perform any method of Examples 45-66.

Example 68 is at least one machine readable medium to implement tracking food contamination using computer vision and a sensor array, the at least one machine readable medium including instructions that, when executed by a machine, cause the machine to perform any method of Examples 45-66.

Example 69 is a system for tracking food contamination using computer vision and a sensor array, the system comprising: means for identifying that a food item has moved to a monitored area using the computer vision; means for obtaining sensor readings from the sensor array; means for determining a potential contamination of the food item using the sensor readings; means for associating the potential contamination of the food item with a contamination area in the monitoring area using the computer vision; and; means for outputting, for display in the contamination area, a notification indicating the potential contamination.

In Example 70, the subject matter of Example 69 optionally includes the means for identifying that the food item has moved into the monitored area using computer further comprising: means for obtaining an image from a camera positioned to observe the monitored area; means for comparing the image to a set of images of food items, the set of images of food items including an image of the food item; means for selecting the food item based on the comparison; and means for identifying that the food item has moved to the monitored area based on the selection.

In Example 71, the subject matter of any one or more of Examples 69-70 optionally include means for selecting a ruleset for the food item from a set of food specific rulesets; means for comparing the sensor readings to the ruleset for the food item; and means for determining the potential contamination based on the comparison.

In Example 72, the subject matter of Example 71 optionally includes means for obtaining an image of the monitored area from a camera; means for determining the contamination area for the potential contamination using the selected ruleset; and means for associating the contamination area with a subsection of the image.

In Example 73, the subject matter of any one or more of Examples 71-72 optionally include means for identifying an action of a person handling the food item using the computer vision and the sensor readings; means for determining that the action violates a rule of the ruleset for the food item; and means for modifying the rule by processing the violation of the rule using machine learning.

In Example 74, the subject matter of any one or more of Examples 71-73 optionally include wherein the means for selecting a ruleset for the food item from a set of food specific rulesets comprises: means for identifying a person handling the food item using the computer vision; means for determining a user profile for the person handling the food item; and means for selecting the ruleset in part based on the user profile.

In Example 75, the subject matter of any one or more of Examples 71-74 optionally include wherein the means for selecting a ruleset for the food item from a set of food specific rulesets comprises: means for identifying a person for whom the food item is being prepared using the computer vision; means for determining a user profile for the person for whom the food item is being prepared; and means for selecting the ruleset in part based on the user profile.

In Example 76, the subject matter of any one or more of Examples 71-75 optionally include means for identifying that an object has contacted the food item using the computer vision and the sensor readings; means for associating the potential contamination with the object; means for determining that the object has made contact with a another food item in violation of a rule of the ruleset for the food item; means for storing an indication of the violation of the rule; and means for outputting a message indicating the violation to a surface near the object.

In Example 77, the subject matter of any one or more of Examples 71-76 optionally include means for selecting a food temperature rule from the ruleset for the food item; means for determining the temperature of the food item over a time period using the sensor readings; means for calculating a rate of temperature change for the food item over the time period; means for calculating a contamination time for the food item using the rate of temperature change for the food item; and means for transmitting, for display in the contamination area, a message including the contamination time for the food item.

In Example 78, the subject matter of any one or more of Examples 69-77 optionally include means for identifying a first action performed in response to the notification; means for comparing the first action performed with an action model for the notification; and means for transmitting a message indicating a second action to be performed based on the comparison.

In Example 79, the subject matter of any one or more of Examples 69-78 optionally include means for identifying that the food item is nearing the potential contamination using the sensor array; and means for transmitting a message including instructions for avoiding the potential contamination.

In Example 80, the subject matter of any one or more of Examples 69-79 optionally include means for capturing an image of the food item using a camera; means for identifying the food item is nearing the potential contamination using the image of the food item; and means for transmitting a message including instructions for avoiding the potential contamination.

In Example 81, the subject matter of any one or more of Examples 69-80 optionally include means for identifying a storage area of the food item; means for obtaining a set of environmental sensor measurements for the storage area; means for determining that the food item is in a pre-contaminated state using the set of environmental sensor measurements; and means for transmitting a message including instructions for removing the food item from the pre-contaminated state.

In Example 82, the subject matter of any one or more of Examples 69-81 optionally include wherein the notification is output as a projection in the contaminated area.

In Example 83, the subject matter of any one or more of Examples 69-82 optionally include wherein the sensor readings are obtained via a wireless network.

In Example 84, the subject matter of any one or more of Examples 69-83 optionally include wherein the means for obtaining sensor readings from the sensor array comprises: means for obtaining a food surface temperature from a thermometer in the sensor array.

In Example 85, the subject matter of any one or more of Examples 69-84 optionally include wherein the means for obtaining sensor readings from the sensor array comprises: means for obtaining an environmental relative humidity from humidity sensor in the sensor array.

In Example 86, the subject matter of any one or more of Examples 69-85 optionally include wherein the means for obtaining sensor readings from the sensor array comprises: means for obtaining a food bacteria count from a bacteria sensor in the sensor array.

In Example 87, the subject matter of any one or more of Examples 69-86 optionally include wherein the means for obtaining sensor readings from the sensor array comprises: means for obtaining a food gas measurement from a gas sensor in the sensor array.

In Example 88, the subject matter of any one or more of Examples 69-87 optionally include wherein the means for obtaining sensor readings from the sensor array comprises: means for obtaining a food surface temperature from an infrared camera in the sensor array.

In Example 89, the subject matter of any one or more of Examples 69-88 optionally include wherein the means for obtaining sensor readings from the sensor array comprises: means for obtaining a food radiation count from a radiation sensor in the sensor array.

In Example 90, the subject matter of any one or more of Examples 69-89 optionally include wherein the means for obtaining sensor readings from the sensor array comprises: means for obtaining an indication of food contact from a contact sensor in the sensor array.

Example 91 is at least one machine-readable medium including instructions, which when executed by a machine, cause the machine to perform operations of any of the operations of Examples 1-90.

Example 92 is an apparatus comprising means for performing any of the operations of Examples 1-90.

Example 93 is a system to perform the operations of any of the Examples 1-90.

Example 94 is a method to perform the operations of any of the Examples 1-90.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is to allow the reader to quickly ascertain the nature of the technical disclosure and is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the embodiments should be determined with reference to the appended claims, along with the full scope of equivalents to which such claims are entitled.

What is claimed is:

1. A system for tracking food contamination using computer vision and a sensor array, the system comprising:
    at least one processor;
    machine readable media including instructions that, when executed by the at least one processor, cause the at least one processor to:
    identify that a food item has moved to a monitored area using the computer vision;
    obtain sensor readings from the sensor array;
    determine a potential contamination of the food item using the sensor readings;
    associate the potential contamination of the food item with a contamination area in the monitoring area using the computer vision; and;
    output, for display within the contamination area, a notification indicating a surface area of the potential contamination, wherein the notification includes projecting a grid on the potential contamination that defines the surface area of the potential contamination.

2. The system of claim 1, the instructions to identify that the food item has moved into the monitored area using the computer vision further comprising instructions to:
    obtain an image from a camera positioned to observe the monitored area;
    compare the image to a set of images of food items, the set of images of food items including an image of the food item;
    select the food item based on the comparison; and
    identify that the food item has moved to the monitored area based on the selection.

3. The system of claim 1, further comprising instructions to:
    select a ruleset for the food item from a set of food specific rulesets;
    compare the sensor readings to the ruleset for the food item; and
    determine the potential contamination based on the comparison.

4. The system of claim 3, further comprising instructions to:

obtain an image of the monitored area from a camera;
determine the contamination area for the potential contamination using the selected ruleset; and
associate the contamination area with a subsection of the image.

5. The system of claim 3, further comprising instructions to:
identify an action of a person handling the food item using the computer vision and the sensor readings;
determine that the action violates a rule of the ruleset for the food item; and
modify the rule by processing the violation of the rule using machine learning.

6. The system of claim 3, wherein the instructions to select a ruleset for the food item from a set of food specific rulesets comprises instructions to:
identify a person for whom the food item is being prepared using the computer vision;
determine a user profile for the person for whom the food item is being prepared; and
select the ruleset in part based on the user profile.

7. The system of claim 3, further comprising instructions to:
identify that an object has contacted the food item using the computer vision and the sensor readings;
associate the potential contamination with the object;
determine that the object has made contact with a another food item in violation of a rule of the ruleset for the food item;
store an indication of the violation of the rule; and
output a message indicating the violation to a surface near the object.

8. The system of claim 3, further comprising instructions to:
select a food temperature rule from the ruleset for the food item;
determine the temperature of the food item over a time period using the sensor readings;
calculate a rate of temperature change for the food item over the time period;
calculate a contamination time for the food item using the rate of temperature change for the food item; and
transmit, for display in the contamination area, a message including the contamination time for the food item.

9. The system of claim 1, further comprising instructions to:
identify a first action performed in response to the notification;
compare the first action performed with an action model for the notification; and
transmit a message indicating a second action to be performed based on the comparison.

10. The system of claim 1, further comprising instructions to:
identify that the food item is nearing the potential contamination using the sensor array; and
transmit a message including instructions for avoiding the potential contamination.

11. The system of claim 1, further comprising instructions to:
capture an image of the food item using a camera;
identify the food item is nearing the potential contamination using the image of the food item; and
transmit a message including instructions for avoiding the potential contamination.

12. The system of claim 1, further comprising instructions to:
identify a storage area of the food item;
obtain a set of environmental sensor measurements for the storage area;
determine that the food item is in a pre-contaminated state using the set of environmental sensor measurements; and
transmit a message including instructions for removing the food item from the pre-contaminated state.

13. At least one non-transitory machine readable medium including instructions for tracking food contamination using computer vision and a sensor array that, when executed by a machine, cause the machine to:
identify that a food item has moved to a monitored area using the computer vision;
obtain sensor readings from the sensor array;
determine a potential contamination of the food item using the sensor readings;
associate the potential contamination of the food item with a contamination area in the monitoring area using the computer vision; and;
output, for display within the contamination area, a notification indicating a surface area of the potential contamination, wherein the notification includes projecting a grid on the potential contamination that defines the surface area of the potential contamination.

14. The at least one machine readable medium of claim 13, the instructions to identify that the food item has moved into the monitored area using the computer vision further comprising instructions to:
obtain an image from a camera positioned to observe the monitored area;
compare the image to a set of images of food items, the set of images of food items including an image of the food item;
select the food item based on the comparison; and
identify that the food item has moved to the monitored area based on the selection.

15. The at least one machine readable medium of claim 13, further comprising instructions to:
select a ruleset for the food item from a set of food specific rulesets;
compare the sensor readings to the ruleset for the food item; and
determine the potential contamination based on the comparison.

16. The at least one machine readable medium of claim 15, further comprising instructions to:
identify an action of a person handling the food item using the computer vision and the sensor readings;
determine that the action violates a rule of the ruleset for the food item; and
modify the rule by processing the violation of the rule using machine learning.

17. The at least one machine readable medium of claim 15, wherein the instructions to select a ruleset for the food item from a set of food specific rulesets comprises instructions to:
identify a person handling the food item using the computer vision;
determine a user profile for the person handling the food item; and
select the ruleset in part based on the user profile.

18. The at least one machine readable medium of claim 15, further comprising instructions to:
select a food temperature rule from the ruleset for the food item;

determine the temperature of the food item over a time period using the sensor readings;
calculate a rate of temperature change for the food item over the time period;
calculate a contamination time for the food item using the rate of temperature change for the food item; and
transmit, for display in the contamination area, a message including the contamination time for the food item.

19. A method for tracking food contamination using computer vision and a sensor array, the method comprising:
identifying that a food item has moved to a monitored area using the computer vision;
obtaining sensor readings from the sensor array;
determining a potential contamination of the food item using the sensor readings;
associating the potential contamination of the food item with a contamination area in the monitoring area using the computer vision; and;
outputting, for display within the contamination area, a notification indicating a surface area of the potential contamination, wherein the notification includes projecting a grid on the potential contamination that defines the surface area of the potential contamination.

20. The method of claim 19, the identifying that the food item has moved into the monitored area using the computer vision further comprising:
obtaining an image from a camera positioned to observe the monitored area;
comparing the image to a set of images of food items, the set of images of food items including an image of the food item;
selecting the food item based on the comparison; and
identifying that the food item has moved to the monitored area based on the selection.

21. The method of claim 19, further comprising:
selecting a ruleset for the food item from a set of food specific rulesets;
comparing the sensor readings to the ruleset for the food item; and
determining the potential contamination based on the comparison.

22. The method of claim 21, further comprising:
identifying that an object has contacted the food item using the computer vision and the sensor readings;
associating the potential contamination with the object;
determining that the object has made contact with a another food item in violation of a rule of the ruleset for the food item;
storing an indication of the violation of the rule; and
outputting a message indicating the violation to a surface near the object.

23. The method of claim 21, further comprising:
selecting a food temperature rule from the ruleset for the food item;
determining the temperature of the food item over a time period using the sensor readings;
calculating a rate of temperature change for the food item over the time period;
calculating a contamination time for the food item using the rate of temperature change for the food item; and
transmitting, for display in the contamination area, a message including the contamination time for the food item.

24. The method of claim 19, further comprising:
identifying a first action performed in response to the notification;
comparing the first action performed with an action model for the notification; and
transmitting a message indicating a second action to be performed based on the comparison.

* * * * *

UNITED STATES PATENT AND TRADEMARK OFFICE
CERTIFICATE OF CORRECTION

PATENT NO. : 10,275,659 B2
APPLICATION NO. : 15/475423
DATED : April 30, 2019
INVENTOR(S) : Shi et al.

Page 1 of 1

It is certified that error appears in the above-identified patent and that said Letters Patent is hereby corrected as shown below:

In the Claims

In Column 26, Line 41, in Claim 1, delete "and;" and insert --and-- therefor

In Column 28, Line 21, in Claim 13, delete "and;" and insert --and-- therefor

In Column 29, Line 19, in Claim 19, delete "and;" and insert --and-- therefor

Signed and Sealed this
Twenty-sixth Day of January, 2021

Drew Hirshfeld
*Performing the Functions and Duties of the
Under Secretary of Commerce for Intellectual Property and
Director of the United States Patent and Trademark Office*